(12) United States Patent
Abbott-Beauregard et al.

(10) Patent No.: US 12,377,190 B2
(45) Date of Patent: Aug. 5, 2025

(54) ACOUSTICALLY RESPONSIVE BIOMATERIALS

(71) Applicant: CARNEGIE MELLON UNIVERSITY, Pittsburgh, PA (US)

(72) Inventors: Rosalyn Abbott-Beauregard, Pittsburgh, PA (US); Megan Debari, Pittsburgh, PA (US)

(73) Assignee: CARNEGIE MELLON UNIVERSITY, Pittsburgh, PA (US)

( * ) Notice: Subject to any disclaimer, the term of this patent is extended or adjusted under 35 U.S.C. 154(b) by 0 days.

(21) Appl. No.: 18/554,058

(22) PCT Filed: Apr. 26, 2022

(86) PCT No.: PCT/US2022/026271
§ 371 (c)(1),
(2) Date: Oct. 5, 2023

(87) PCT Pub. No.: WO2022/232090
PCT Pub. Date: Nov. 3, 2022

(65) Prior Publication Data
US 2024/0366835 A1     Nov. 7, 2024

Related U.S. Application Data

(60) Provisional application No. 63/181,601, filed on Apr. 29, 2021.

(51) Int. Cl.
*A61K 36/00* (2006.01)
*A61L 27/22* (2006.01)
*A61L 27/36* (2006.01)
*D01F 4/02* (2006.01)

(52) U.S. Cl.
CPC ......... *A61L 27/227* (2013.01); *A61L 27/3604* (2013.01); *A61L 27/3687* (2013.01); *D01F 4/02* (2013.01)

(58) Field of Classification Search
None
See application file for complete search history.

(56) References Cited

U.S. PATENT DOCUMENTS

| | | |
|---|---|---|
| 2011/0171239 A1 | 7/2011 | Kaplan |
| 2014/0308362 A1 | 10/2014 | Bellas |
| 2014/0364381 A1 | 12/2014 | Ju |
| 2015/0322122 A1 | 11/2015 | Fraser |
| 2018/0185096 A1 | 7/2018 | Eisenfrats |
| 2019/0142529 A1 | 5/2019 | Crunick |
| 2019/0192377 A1 | 6/2019 | Kaila |
| 2020/0306415 A1 | 10/2020 | Kaplan |

FOREIGN PATENT DOCUMENTS

| | | |
|---|---|---|
| WO | 2019094700 A1 | 5/2019 |
| WO | 2022232090 A2 | 11/2022 |

OTHER PUBLICATIONS

International Search Report and Written Opinion for International Application No. PCT/US2022/026271, mailed Oct. 5, 2022, 13 pages.
Apfel et al., "Gauging the Likelihood of Cavitation From Short-Pulse, Low-Duty Cycle Diagnostic Ultrasound," Ultrasound in Med & Biol., vol. 17, No. 2: 179-185 (1991).
Fan et al., "Submicron-Bubble-Enhanced Focused Ultrasound for Blood-Brain Barrier Disruption and Improved CNS Drug Delivery," PLoS One, vol. 9, Issue 5: e96327 (May 2014).
Samal et al., "Ultrasound Sonication Effects on Silk Fibroin Protein," Macromolecular Materials and Engineering, vol. 298: 1201-1208 (2013).

*Primary Examiner* — Russell G Fiebig
(74) *Attorney, Agent, or Firm* — KDW FIRM PLLC

(57) ABSTRACT

A method and apparatus for degrading a hypodermal tissue scaffold involves exposing the scaffold to a low-intensity focused ultrasonic beam such as to burst gas vesicles trapped in the silk fibroin from which scaffold is constructed. The rate of degradation van be controlled using ultrasonic beams of varying intensities. In one embodiment, the ultrasonic beams are administered trans-dermally to a hypodermal scaffold.

10 Claims, 15 Drawing Sheets

| Functional Group | Silk I Range (cm⁻¹) | Silk II Range (cm⁻¹) |
|---|---|---|
| Amide I | 1,648-1,654 | 1,610-1,630 |
| Amide III | 1,535-1,542 | 1,510-1,520 |

FIG. 9(A)

| Condition | Secondary Structure (IR Range cm⁻¹) | | | | |
|---|---|---|---|---|---|
| | β Sheet (1703-1697, 1637-1616) | β Turn (1696-1663) | α Helix (1662-1656) | Random Coils (1655-1638) | Side Chains (1615-1605) |
| Vacuum – 0 min. | 36.00 ± 3.88 | 23.46 ± 5.78 | 7.39 ± 0.87 | 21.06 ± 1.49 | 12.09 ± 1.52 |
| Vacuum – 5 min. | 35.78 ± 2.23 | 23.45 ± 3.82 | 7.47 ± 0.69 | 21.19 ± 1.32 | 12.11 ± 0.80 |
| Vacuum – 10 min. | 35.73 ± 1.13 | 23.88 ± 1.65 | 6.87 ± 0.10 | 20.79 ± 0.60 | 12.71 ± 0.31 |
| Vacuum – 15 min. | 36.03 ± 1.28 | 22.70 ± 1.89 | 6.92 ± 0.28 | 21.44 ± 1.47 | 12.29 ± 1.53 |
| Nonvacuum – 0 min. | 36.58 ± 1.44 | 22.70 ± 2.32 | 6.77 ± 0.15 | 21.14 ± 0.75 | 12.82 ± 0.70 |
| Nonvacuum – 5 min. | 35.43 ± 0.71 | 24.60 ± 0.88 | 6.75 ± 0.07 | 20.46 ± 0.20 | 12.76 ± 0.32 |
| Nonvacuum – 10 min. | 35.70 ± 0.51 | 24.23 ± 0.65 | 6.79 ± 0.03 | 20.63 ± 0.28 | 12.65 ± 0.18 |
| Nonvacuum – 15 min. | 34.11 ± 1.78 | 26.75 ± 2.86 | 6.80 ± 0.11 | 19.81 ± 0.57 | 12.53 ± 0.68 |

FIG. 9(B)

| *FIG. 11(C)* | *FIG. 11(D)* | *FIG. 11(E)* | *FIG. 11(F)* |

ACOUSTICALLY RESPONSIVE BIOMATERIALS

RELATED APPLICATIONS

This application is a national phase filing under 35 U.S.C. § 371 claiming the benefit of and priority to International Patent Application No. PCT/US2022/026271, filed Apr. 26, 2022, entitled "Acoustically Responsive Biomaterials", which claims the benefit of U.S. Provisional Patent Application No. 63/181,601, filed Apr. 29, 2021, the contents of which are incorporated herein in their entireties.

BACKGROUND OF THE INVENTION

Tissue engineering provides a platform for designing tissues and organs that use biomaterials to restore or replace function. One of the goals of tissue engineering is to design the degradation and remodeling kinetics of a biomaterial to: 1) initially support cells to proliferate and secrete matrix, and 2) gradually degrade as de novo tissue replaces the scaffold. In this way, paired tissue remodeling and scaffold degradation can maintain intrinsic properties throughout the healing process.

However, patients have differing regenerative capacities due to complex, interacting, and currently unpredictable factors such as age, disease state, nutritional status, lifestyle, and gender. For example, older patients regenerate tissue more slowly than younger patients, and therefore require scaffolds with slower degradation profiles then younger patients. When scaffolds degrade too quickly in these patients, there are negative effects, such as low cell numbers and a lack of angiogenesis. On the other hand, younger patients require fast degrading biomaterials to reduce the chance of an inappropriate immune response or biofilm formation.

Silk fibroin is a strong candidate for use in constructing tissue scaffolds for tissue regenerative applications due to its tunable degradation profile and mechanical properties. Factors such as the crystallinity, pore size, fibroin concentration, and structural stability all affect the timeline of scaffold degradation, which can range from hours to years. Silk fibroin is also considered biocompatible, with minimal immunogenic effects on a number of different cell types.

Current strategies of designing one-size-fits-all biomaterials, in particular, biomaterials composed of silk fibroin, is ineffective for many patients. To improve biomaterial integration, a method for tuning degradation that can be triggered non-invasively, post-implantation would be ideal. Because regeneration of tissue cannot be predicted prior to biomaterial implantation, there is a need for a way to adapt and personalize degradation profiles to improve regenerative outcomes.

SUMMARY OF THE INVENTION

Disclosed herein are methods of altering the degradation profile of scaffolds composed of silk fibroin biomaterials non-invasively, post-implantation through the use of therapeutic ultrasound. This invention describes methods of constructing silk biomaterials that acoustically degrade in response to non-invasive therapeutic ultrasound. One application of this technology comprises acoustically responsive scaffolds for tissue regeneration. In one embodiment, the scaffolds are used alone, implanted in a desired location, and exposed to therapeutic ultrasound to accelerate degradation. In other embodiments, the scaffolds can be combined with cells that could include, but are not limited to, adipose stem cells, adipocytes, mesenchymal stem cells, osteoblasts, chondrocytes, etc. In yet another embodiment, silk microspheres containing drugs can be infused into the scaffolds and can be targeted to trigger the release of drugs at specific locations and at specific times. Various applications of the described methods include, but are not limited to, the repair of volumetric loss of muscle and other soft tissue, breast reconstruction, bone repair, cartilage repair and targeted drug delivery.

The scaffolds are composed primarily of a silk biomaterial, for example, silk fibroin. In a first embodiment, ultrasound induced transient cavitation, that is, the destruction of microbubbles on the scaffold surface, can be used as a mechanism for changing the degradation profile of the silk fibroin. This method is safe for human cells, having no known negative effects on cell viability or metabolism. The effect can be triggered via sonication through human skin, which increases the clinical relevance of the invention. In a second embodiment of the invention, gas vesicles are mixed into a silk fibroin solution during scaffold manufacture. Application of the ultrasound causes the gas vesicles to cavitate and burst, thereby initiating the degradation of the silk fibroin. The second embodiment provides a more controlled process because the rate at which the vesicles burst is dependent on the size of the vesicles and the pressure applied by the ultrasound.

Unlike imaging ultrasound, therapeutic ultrasound often has higher intensities and lower frequencies. For example, high-intensity focused ultrasound (HIFU) has been used clinically to ablate kidney stones, fibroids, and cranial tumors. HIFU generates temperatures that cause damage to cells and proteins. Alternatively, low-intensity focused ultrasound (LIFU) is considered harmless and safe for cells and has been used to disrupt the blood brain barrier by using microbubble interactions. According to FDA regulations, diagnostic ultrasound applications with a mechanical index lower than 1.9 are considered safe and are approved for use.

A reduction in the weight of silk scaffolds after non-invasive LIFU sonication was observed. This non-invasive outcome was used to optimize the ultrasound settings. The mechanism for ultrasound degradation of silk scaffolds was also determined as being cavitation-induced micro-jets. In addition, the effect of LIFU on cell metabolism/viability and enzymatic degradation was evaluated. Because the desired outcome of the invention is its use to trigger degradation based on monitoring scaffold properties in vivo, it was also determined if changes in degradation of the scaffolds could be detected by 2D greyscale imaging.

BRIEF DESCRIPTION OF THE DRAWINGS

FIG. 9(A) is a table showing the ranges for characteristic functional groups for the scaffoldings.

FIG. 9(B) is a table showing the percentage of secondary structure components of the scaffoldings.

FIGS. 10(C-D) are scaffolds stained with green and red dye to indicate live and dead cells in a sonicated and control group of scaffolds, respectively.

FIGS. 11(C-F) are ultrasound images from each group shown in the graph of FIG. 11(A).

DETAILED DESCRIPTION

Ultrasound can cause transient cavitation within the domain of the scaffold. In a first embodiment of the invention, the transient cavitation causes the collapse of microbubbles already present on the hydrophobic domains of the scaffolds. During the compression phase of the ultrasound wave, bubbles collapse rapidly on themselves. This implosion causes a localized shock wave to propagate away from the collapsed bubble. When this occurs near a solid surface, a high-speed liquid microjet often occurs. When bubbles collapse near a solid surface they quickly lose their spherical symmetry. The side of the bubble away from the surface will push into and through the gas bubble and strike the solid surface with high energy.

In a second embodiment of the invention, the transient cavitation causes gas vesicles present in the domain of the scaffold to burst and collapse, thereby releasing the contents of the vesicles to initiate the localized shockwave. The localized shockwave causes the degradation by striking the surface of the silk fibroin with high energy pulses released by the bursting of the gas vesicles. Additionally, the collapsed gas vesicles increase the porosity of the scaffold. Hydrophobic surfaces can trap gases and form microbubbles. As silk has hydrophobic domains, microbubbles are naturally present on silk scaffolds in aqueous environments. As a proof-of-concept that transient cavitation is the mechanism responsible for the degradation associated with sonication, experiments were conducted on an experimental group. For each time point investigated, a group of scaffolds from a common batch were placed under vacuum in a desiccator prior to sonication. Under vacuum, the microbubbles in the scaffold were removed. This reduction in microbubble concentration limited the number of sites where transient cavitation could occur. Thus, a difference could be observed between the vacuumed group and the non-vacuumed group due to the triggering of transient cavitation.

After ultrasound parameters were finalized, as discussed later herein, weight and porosity were measured before and after sonication. Both methods were non-destructive and allowed for further testing to be performed on the scaffolds. To account for any damage from handling, the experimental groups were normalized to a non-sonicated control (0 min).

In general, non-vacuumed scaffolds exhibited a greater change in weight, porosity, and surface appearance after sonication than vacuumed scaffolds, indicating that cavitation induced by LIFU is the mechanism of silk degradation.

Figure 2:
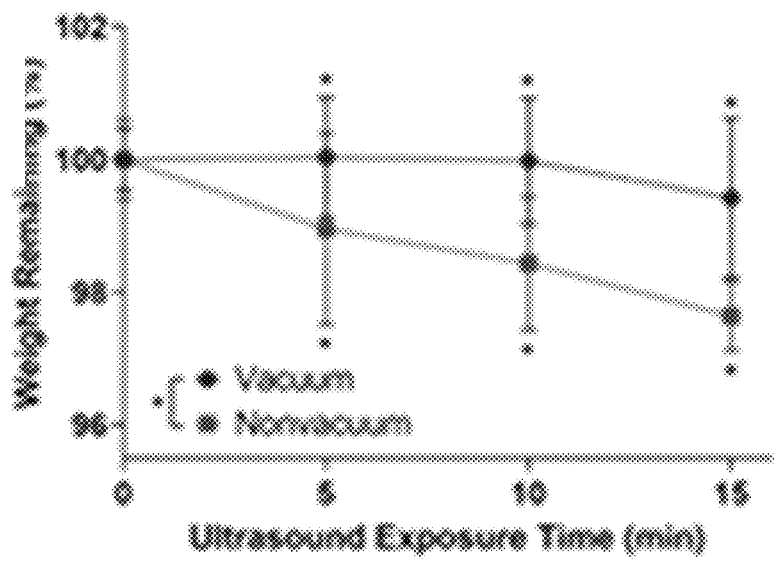
FIG. 2 is a graph showing the difference in weight loss between vacuumed and non-vacuumed scaffoldings as a function of ultrasound exposure time.

As the length of ultrasound exposure increases, there is an increase in scaffold weight loss, as shown in FIG. 2. In particular, there is a significantly greater weight loss in the non-vacuumed samples (where microbubbles are present) than in the vacuumed samples (where microbubbles are removed) starting at 10 minutes of ultrasound exposure. Increasing the sonication time resulted in a significant decrease in the weight of silk scaffolds (8 mm diameter×2 mm height), with non-vacuumed samples exhibiting significantly more weight loss than vacuumed samples with increasing ultrasound exposure time. The greatest weight loss was observed in the non-vacuumed group after 15 minutes of ultrasound exposure.

The non-vacuumed group experienced a steady decrease in weight as the exposure length increased, where there is a linear relationship between weight and ultrasound exposure length. The slope of this line was determined to be significantly non-zero using a linear regression and an F test. While not significant, the small weight loss experienced by the vacuumed samples after 15 minutes of sonication is likely due to residual remaining microbubbles in these samples that were not able to be removed by the vacuuming process. As No quantification of microbubble concentration was performed, a small portion of microbubbles could have persisted after the scaffolds were placed under vacuum.

Figure 3:
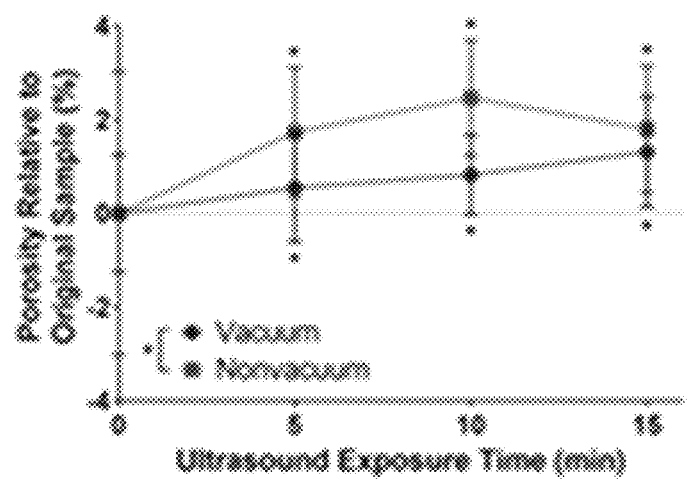
FIG. 3 is a graph showing the difference in porosity between vacuumed and non-vacuumed scaffoldings as a function of ultrasound exposure time.

As expected, when the scaffold weight decreased with longer ultrasound exposure times, the porosity of the scaffolds increased, as shown in FIG. 3. Enhanced porosity (relative to the original sample) with increasing ultrasound exposure time was observed (N=12 for each group). In sensitivity analyses of the mixed effects model, a separate model specific to porosity demonstrated significant increases for each ultrasound time period and a significant difference between vacuumed samples versus non-vacuumed, where non-vacuumed samples had the largest increase in porosity. Asterisks (*) indicate statistical significance ($p<0.05$) from the 0-minute timepoint. There was a significant difference in porosity between the non-vacuumed and vacuumed samples when sonicated for 10 minutes, suggesting the presence of microbubbles enhanced ultrasound effects on porosity at this time point. While the 15-minute timepoint was not statistically different between non-vacuumed and vacuumed groups, sonication increased porosity at all exposure time points.

Figure 4A:
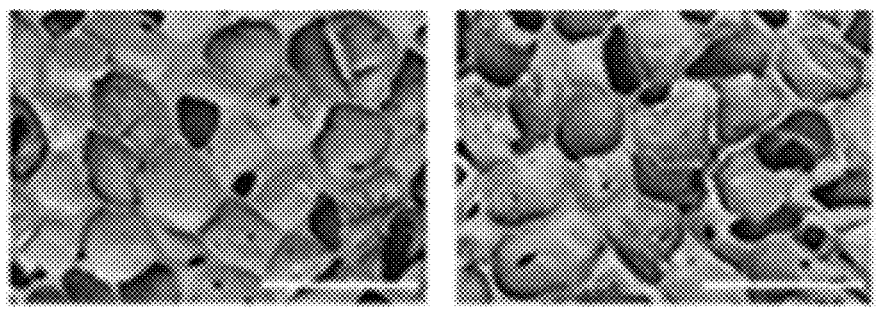
FIG. 4(A-D) are SEM images of vacuumed and non-vacuumed scaffoldings after being exposed to ultrasound for varying time.

To visualize structural differences caused by sonication, scanning electron microscopy (SEM) was used. FIG. 4(A) shows differences between a vacuumed control sample (left) and a vacuumed sonicated sample (right), sonicated for 15 minutes. The surface density is the same in both groups, however some of the pore walls have begun to curl and there are a ruptures and tears in the sonicated scaffold. The slight increase in pore connectivity from this minimal degradation is consistent with the increased porosity noted after 15 minutes of sonication.

Figure 4B:
Figure 4C:
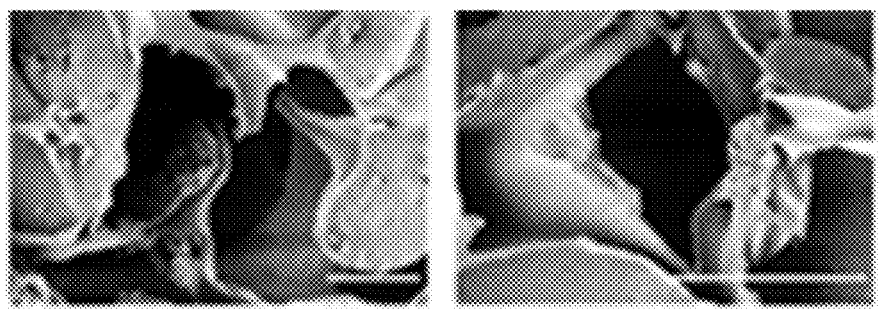
Figure 4D:
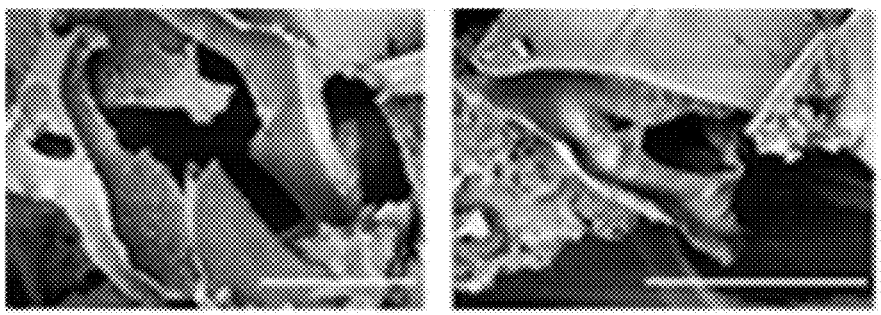

FIG. 4(B) shows non-vacuumed samples containing microbubbles, in which more drastic differences between the control sample (left) and the sonicated sample (right), with 15 minutes of sonication, were observed. The non-vacuumed sonicated scaffolds have a substantial amount of degradation at the surface, with torn walls and a lower surface density. Higher magnification images of the non-vacuumed samples exposed to 15 minutes of sonication, shown in FIGS. 4(C,D), show fragments of the silk scaffold have very clearly been torn or removed from the surface. The images show degradation of the pore walls including tears and rupture points. Scale bars represent 1 mm (C-F) and 200 μm (G-J).

Figure 5A:
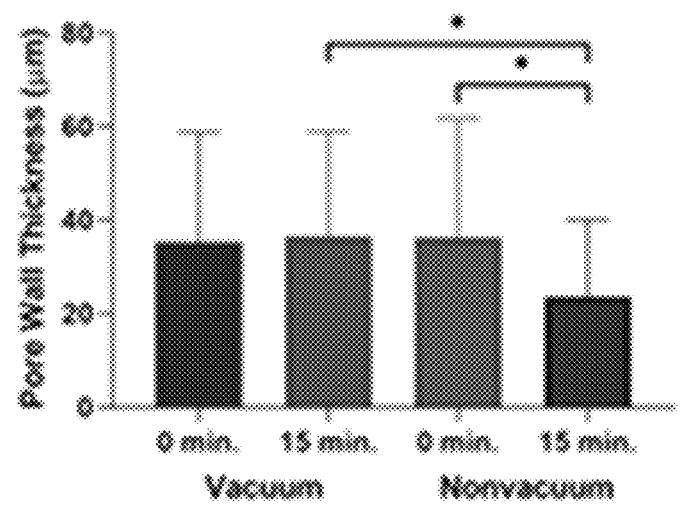
FIG. 5(A) is a graph showing that differences in the pore wall thickness of vacuumed and non-vacuumed scaffoldings as a function of exposure time.
Figure 5B:
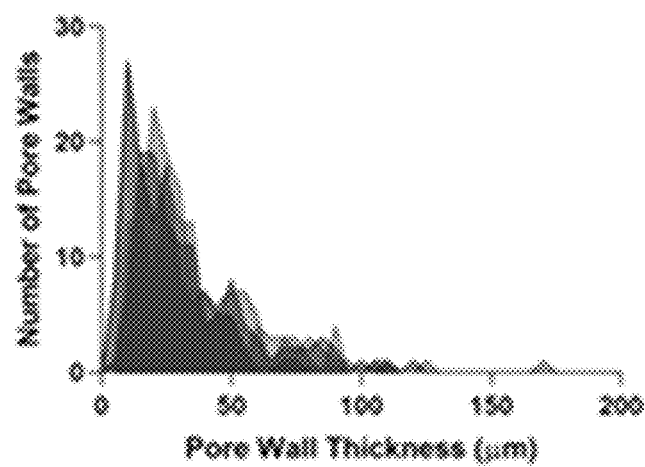
FIG. 5(B) is a histogram showing the range and distribution of pore wall measurements.

The pore wall thickness of these samples was quantified, as shown in the graph of FIGS. 5(A), indicating that 15 minutes of sonication resulted in thinner walls. Pore walls were thinner in the non-vacuumed samples sonicated for 15 minutes compared to the non-vacuumed control. FIG. 5(B) is a histogram showing the range and distribution of pore wall measurements. Experiments were performed in duplicate with independently fabricated scaffolds. Asterisks (*) indicated statistical significance ($p<0.05$). Error bars represent standard deviation. This is likely the reason why the pore walls curl in the sonicated samples. These findings support the trends seen in the weight and porosity data of the non-vacuumed sonicated samples. It is important to note that there does not appear to be a difference between the two control groups. This suggests that putting the scaffolds under vacuum had no effect on the surface structure.

Because the non-vacuumed scaffolds experienced statistically significant weight loss, increases in porosity, and visual degradation that was greater than the vacuumed samples it was concluded that the presence of microbubbles was required for silk degradation. Collectively, the data suggests that mechanical forces from transient cavitation, resulting in microbubbles collapsing, tore the pore walls, decreasing the weight of the scaffolds, and increasing the porosity, showing that transient cavitation is responsible for the degradation caused to the scaffolds during sonication.

Figure 1A:
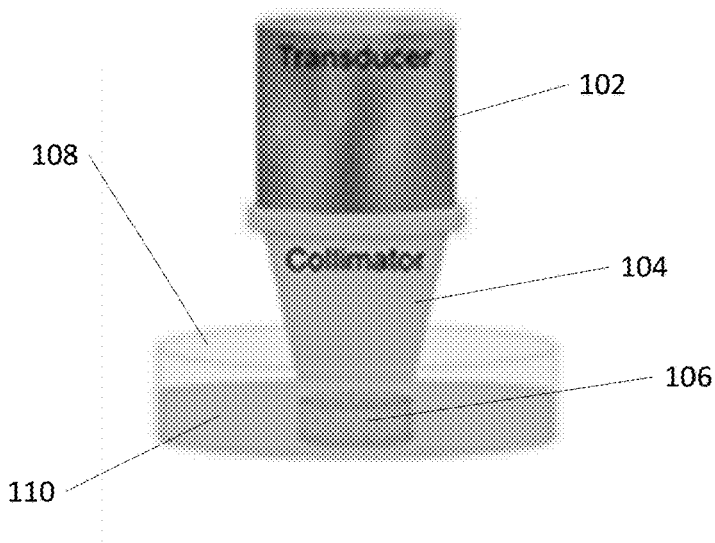
FIG. 1(A) is a schematic of an apparatus used in the proof-of-concept experiments discussed herein.

FIG. 1(A) is a schematic showing the sonication setup for initiating degradation of the scaffolds. The collimator 104 was filled with ultrasound transmission gel to ensure ultrasound waves reached the silk scaffold 106. The collimator 104 was used to space the transducer 102 a focal length away from the scaffolds 106. The silk scaffold 106 was also covered in ultrasound transmission gel 110.

Figure 1B:
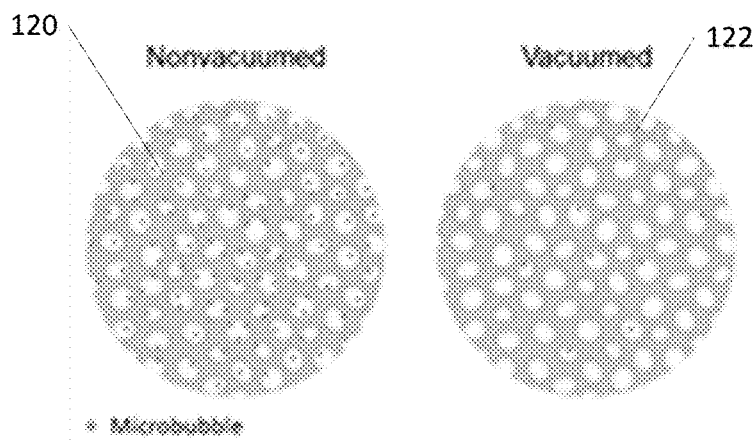
FIG. 1(B) is a schematic representation of vacuumed and non-vacuumed silk scaffoldings.
Figure 1C:
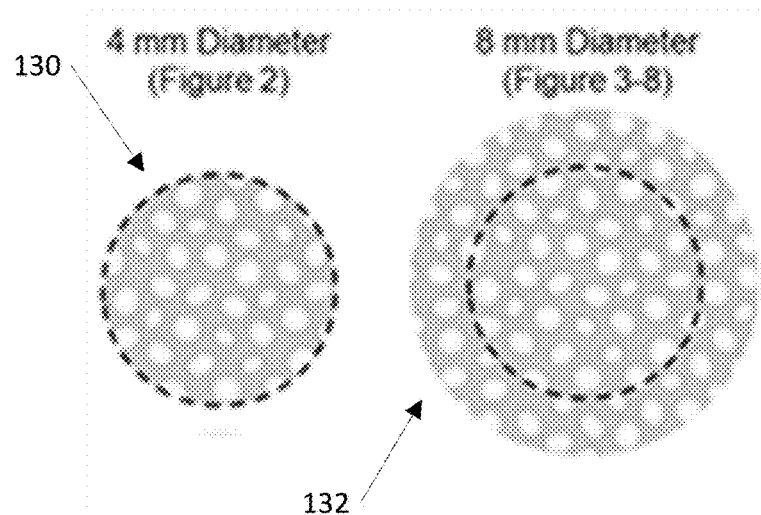
FIG. 1(C) is a schematic representation of a size comparison of the scaffolds used in the proof-of-concept experiments discussed herein.

For mechanical studies, scaffolds 106 were placed under a vacuum to remove microbubbles. Thus, this group is referred to herein as "vacuumed" 122, as shown in FIG. 1(B) herein. Microbubbles are represented by the dots while the ovals represent pores present in the silk scaffolds. As shown in FIG. 1(C), two different scaffold dimensions were used in experiments. Ultrasound settings were determined using 4 mm scaffolds 130, all other experiments were done with 8 mm scaffolds 132. The black dashed circle on the 8 mm scaffold 132 shows the area the ultrasound affected. Because the collimator 104 narrowed the ultrasonic beam to a 4 mm field, only 25% of the 8 mm scaffolds 132 were affected by ultrasound waves.

Scaffold Preparation

Figure 14:
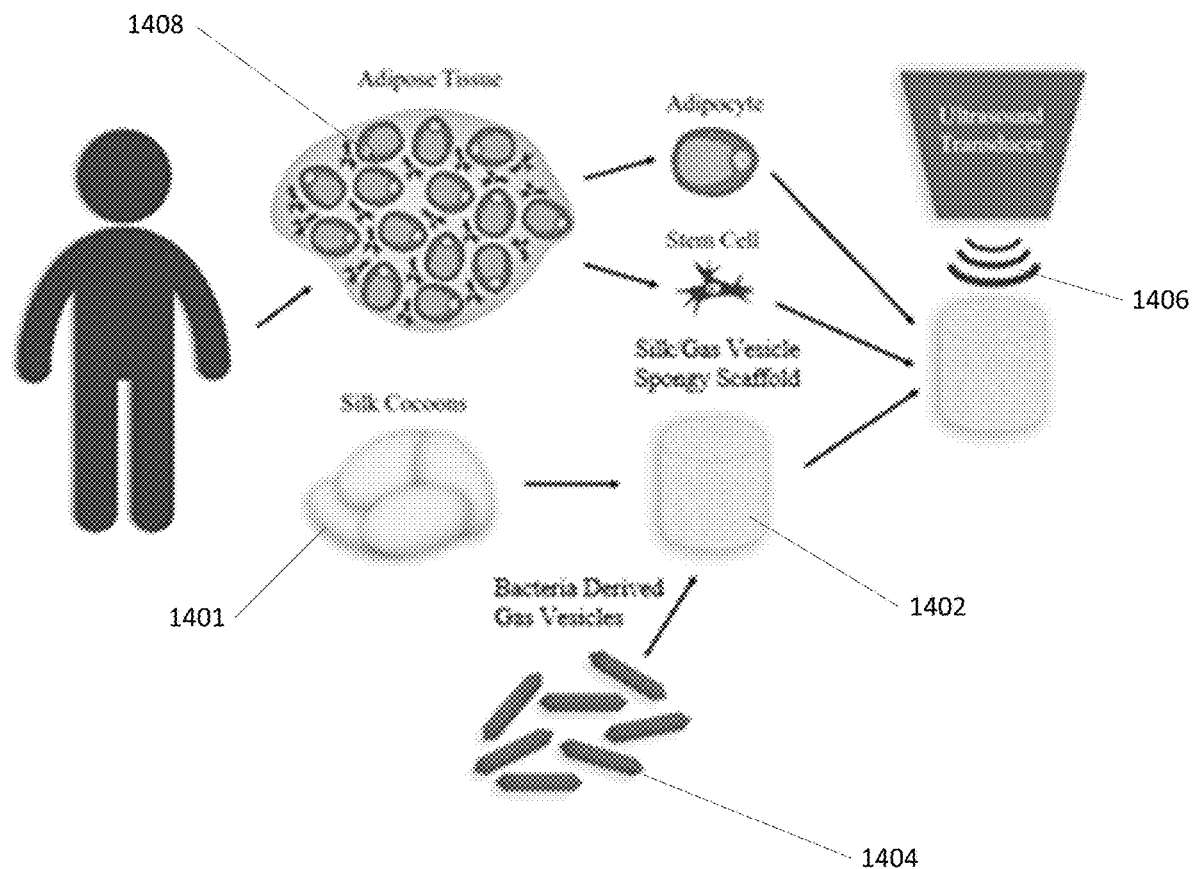
FIG. 14 illustrates the process of the creating the second embodiment of the scaffold using gas vesicles.

Silk fibroin solutions are prepared using silk cocoons 1401, shown in FIG. 14, which are produced, in one embodiment, by *Bombyx mori* silkworms. The cocoons 1401 are cut into small pieces and boiled in an aqueous alkali solution of sodium carbonate ($Na_2CO_3$), urea, citric acid, sodium oleate, etc. for approximately 30 minutes to degum the fibroin fibers. The remaining fibers are rinsed and allowed to dry overnight in ambient conditions. An alternative method to degum the fibroin fibers is to soak the cocoon pieces in an NaOH solution for 24 hours at room temperature. The remaining fibers are rinsed and allowed to dry overnight in ambient conditions. The dry fibroin is then dissolved in an aqueous solution of lithium bromide (LiBr) at approximately 60° C. for 4 hours. This solution is then placed into a set of dialysis cassettes and spun in ultrapure water for 48 hours. The ultrapure water may be changed up to 6 times over the 48 hour period. The remaining solution is removed from the cassettes and centrifuged at 4° C. and 4800 rpm for 20 minutes. This may be repeated to ensure purity.

Scaffolds 106 were then prepared. Aqueous silk is lyophilized and then dissolved in a 17% hexafluoro isopropanol silk solution overnight. The solution is poured over sodium chloride (NaCl) crystals with diameters between 500 and 600 μm. The containers are sealed for 24 hours. After the silk permeates through the salt crystals in the container, they are opened and allowed to dry for 24 hours. The dried scaffolds are placed in methanol for 24 hours to induce β-sheet formation. After methanol annealing, the scaffolds 106 are dried in a chemical hood for 24 hours. The scaffolds are then rinsed for 2-3 days to remove salt from the pores. Finally, the scaffolds 106 are cut into cylinders of 2 mm height and either 8 mm or 4 mm diameter, as shown in FIG. 1(C).

In the second embodiment of the invention, following dialysis, the silk solution 1402 is mixed with the desired number of gas vesicles 1404, as shown in FIG. 14. Salt (sodium chloride) that has been sifted for the desired size range is poured over the silk/gas vesicle solution 1402 causing gelation. After solidification, the scaffolds are washed to remove salt and a spongy scaffold remains. The scaffolds can be cut to the desired size.

In either embodiment, the scaffolds may be coated or infused with therapeutic cells of various types.

Gas Vesicle Preparation

In one embodiment, to form gas vesicles 1404, a 5% bovine serum albumin (BSA) solution is combined with a 1% silk solution extracted from *Bombyx mori* silkworm cocoons. The solution is placed in an oven at 60° C. for 10 minutes to allow the BSA to fully dissolve and slightly denature the protein (to improve encapsulation). Sodium octanoate and N-acetyl-DL-tryptophan are then added to the solution to create a final 0.08 M solution with respect to both chemicals. To form the gas vesicles 1404, the solution is sonicated 1406. The size distribution of the BSA gas vesicles determines their concentration. In one embodiment, the solution contains approximately 500 million gas vesicles 1404 per mL. The solution is resuspended in a final 6% silk solution. The silk solutions are formed into scaffolds as described previously. The pore size and concentration of gas vesicles can be controlled and optimized for the desired tissue application.

In other embodiments, the gas vesicles 1404 can be derived from bacteria, such as *Anabaena flos-aquae* (Ana) and *Halobacteria salinarum* NRC-1 (Halo). These gas vesicles are naturally made and can be isolated from the bacteria and used as ultrasound contrast agents. Gas vesicles produced by different bacteria have different resistances to pressure-induced collapse or cavitation varying from 50 to 800 kPa. Even gas vesicles 1404 from the same species can collapse at slightly different pressures due to the polydispersity in size resulting in a distribution of collapse pressures. For example, gas vesicles 1404 isolated from Halo bacteria collapse at a mean pressure of 59 kPa, while variants of Ana derived gas vesicles 1404 collapse at 193 kPa and 587 kPa. These are low pressures that can be accomplished without affecting the viability of cells.

The specific pressure needed to burst the gas vesicles 1404 is dependent on the size of the vesicle and, in some cases, the bacteria from which the vesicles are made. Vesicles of various sizes can be present in the scaffold. Therefore, by controlling different ultrasound parameters, such as frequency, pulse duration, pulse frequency, etc., the intensity and pressure required to burst gas vesicles of various sizes can be achieved, and different rates of bursting of the vescicles can be obtained. Currently, biomaterials are designed with set degradation profiles that cannot be personalized once implanted. However, patients regenerate tissue and degrade biomaterials at different rates, so a personalized, non-invasively controllable method of controlling the degradation rate is advantageous. By incorporating gas vesicles 1404 into the biomaterials, local degradation can be induced based on monitoring regenerative outcomes.

Figure 15:
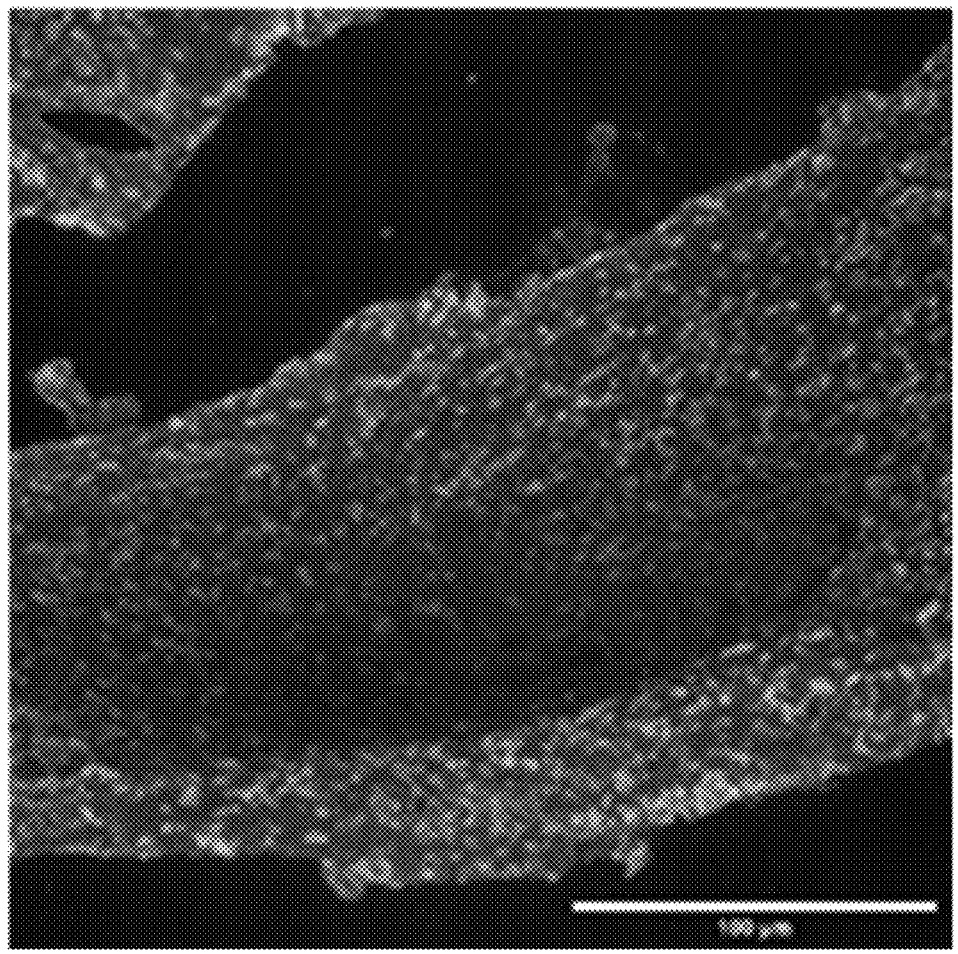
FIG. 15 shows an image of a portion of a scaffold having gas vesicles.

FIG. 15 shows an image of a portion of a scaffold having gas vesicles. The silk fibroin is the darker portions of the image, while the gas vesicles are the lighter portions of the image.

Seeding of Cells onto the Scaffold

In some embodiment, the scaffold can be coated or infused with therapeutic cells. For example, the described embodiment optionally enables tissue regeneration using the recipients' own cells. Human adipose-derived stem cells (hASCs) 1408 can be isolated from surgeries, such as panniculectomy or abdominoplasty surgeries. These cells can then be seeded onto the scaffolds. These cells have the potential to differentiate into adipocytes, chondrocytes, myocytes, osteocytes, epithelial cells, endothelial cells, etc. The cells may fill the majority of the free space within the scaffold. The scaffolds can then be exposed to therapeutic ultrasound to increase the interconnectivity of the pores. The result is more surface area and free area to which the cells can attach. Degradation is accelerated due to the increase in surface area.

Subcutaneous adipose tissue 1408 can be obtained from elective abdominoplasty procedures or lipoaspiration and processed the same day of surgery. For whole tissue (abdominoplasty or panniculectomy procedures), the adipose tissue is cut into small pieces and combined with equal volume of phosphate buffer solution (PBS) containing bovine serum albumin (1%) and collagenase (0.1% type I). The adipose tissue and collagenase solution are incubated for 30-60 minutes (37° C., 5% $CO_2$). Following the incubation step, the solution is centrifuged at 300× g for 5 minutes at room temperature. The step separates the solution into adipocytes and stromal vascular fraction (stem cells, endothelial cells, fibroblasts, pericytes etc.). At this stage adipocytes and stem cells can be isolated.

The isolated cells can be grown in flasks until enough cells are acquired. The cells can then be lifted using trypsin and seeded into the scaffold. The scaffolds are stored in growth media (DMEM growth media, high glucose, 10% fetal bovine serum, 1% penicillin-streptomycin), so proteins bind to the scaffolds to increase cell adhesion. The cells are seeded onto the scaffolds and incubated in growth media to ensure the cells fill the scaffold.

In other embodiments, the scaffolds can be combined with cells other than adipocytes, that could include, but are not limited to, adipose stem cells, mesenchymal stem cells, osteoblasts, chondrocytes, etc.

Ultrasound (Sonication) Settings

The scaffolds 106 (n=96) were placed in ultrapure water 16 hours before ultrasound exposure. Half the scaffolds (n=48) were placed under vacuum for 5 minutes to eliminate air bubbles in the scaffolds 106. In the vacuum group, air bubbles were visibly eluded out of the scaffolds. Vacuumed scaffolds 122, as shown in FIG. 1(B), were used to prove that transient cavitation was responsible for scaffold degradation. The scaffolds 106 were removed from the water, placed on a polystyrene dish 108, and covered in ultrasound transmission gel 110 before exposure, as shown in FIG. 1(A).

Scaffolds 106 were subjected to the cyclic sonication process for varying times (5, 10, and 15 min). Following ultrasound exposure or sonication, the ultrasound gel 110 was rinsed off the scaffolds 106. Scaffolds 106 were placed in ultrapure water for two hours and then spun at 300 RPM in ultrapure water for 60 minutes on a spin plate. The scaffolds 106 were dried in a 60° C. oven overnight. Scaffolds 106 were tested using ATR to ensure the washing steps removed all of the gel.

Results

Weight: Prior to weighing the scaffolds 106 they were dried overnight in an oven at 60° C. The weight of the dry scaffolds was measured before and after ultrasound exposure.

Porosity: The dry scaffolds 106 were weighed (W1), then placed in hexane, and subjected to a vacuum for 5 minutes. Hexane was added to a separate 15 mL polypropylene centrifuge tube and weighted. After vacuuming for 5 minutes, the scaffolds 106 were moved to the 15 mL centrifuge tube and weighed again. The difference between the weight of the centrifuge tube with hexane, and the weight after the scaffold 106 was added, was used for calculations. The density was calculated using the following equation:

$$d = W_1 \bigg/ \left[ \frac{W_2 - W_1}{\rho_h} + \frac{W_1}{\rho_s} \right]$$

The density of silk ($\rho_s$) used in the calculations was 1.348 g/mL and the density of hexane used ($\rho_h$) was 0.659 g/mL. This process was performed for each scaffold and repeated after ultrasound exposure.

Scanning Electron Microscopy (SEM): Samples were placed in an oven at 60° C. for 24 hours. Dry samples (n=2) from each group were coated with 5 nm of platinum. SEM images were taken using backscatter electrons.

Pore Wall Thickness: Wall thicknesses were measured on 50× SEM images. Four scaffolds from the nonvacuumed 0- and 15-min. exposure groups were imaged. 30 pore walls were measured on each image (N=120).

Compressive Modulus: A 10 N load cell was used for compression testing. The scaffolds 106 were placed in ultrapure water 16 hours before testing. The scaffolds 106 were compressed to 80% at a rate of 1 mm/min through three cycles of loading and unloading. The recording of data did not begin until the compressive stress on the scaffold 106 reached 0.001 MPa. The compressive modulus was determined by calculating the slope of the linear region of the stress-strain curve found within the first 30% of compression. The scaffolds were compressed wet. This was performed to better mimic the conditions the scaffolds would be exposed to in vivo.

Attenuated Total Reflection Spectroscopy (ATR): A spectrometer with a universal ATR sampling accessory was used to record measurements. 32 accumulation scans from 650 to 4000 $cm^{-1}$ were recorded per sample. Peaks characteristic of silk's secondary structure (amide I and II) were analyzed to determine peak wavenumber and the ratio of transmittance (using 3277 $cm^{-1}$ as a reference peak) was calculated to determine significant differences. The IR range 1703-1605 $cm^{-1}$ was analyzed to determine the percent of secondary structures ($\beta$ sheet, $\beta$ turn, $\alpha$ helix, random coil, and side chains). Specific ranges were used to correlate the secondary structures. The area of the peaks was determined and used to calculate the percent of each secondary structure present.

Cell Viability

Isolation of human adipose derived stem cells (hASCs): hASCs were isolated from a single female donor (Age: 25, BMI: 33.47, Race: Caucasian) from subcutaneous adipose tissue. The cells were isolated by mechanically blending the adipose tissue and incubating it in a collagenase solution (0.1% collagenase, 1% bovine serum albumin, 98.9% phosphate buffer solution) at a 1:1 ratio. The mixture was placed in a cell culture incubator for 1 hour and then centrifuged to isolate the stromal vascular fraction. The cells were resuspended in media (DMEM with 10% fetal bovine serum and 1×penicillin-streptomycin), centrifuged, and seeded into flasks.

Seeding Scaffolds with hASCs: Silk scaffolds (cylinders, 2 mm height×8 mm diameter) were placed in ultrapure water and autoclaved. The scaffolds were then placed in cell culture media (DMEM, 10% fetal bovine serum, 1% penicillin (10,000 units/mL), 1% streptomycin (10,000 μg/mL)) overnight for protein adsorption to encourage cell adhesion after seeding. Cells were lifted from culture flasks and seeded on to scaffolds at a density of 1,000,000 cells/scaffold. 500,000 cells were seeded on each side of the scaffold. Scaffolds were placed in the incubator for 2 hours and then 1 mL of cell culture media was added to each well. The scaffolds (N=22) were cultured for 2 weeks. This experiment was performed in duplicate.

Resazurin Metabolic Assay: Before and after sonication, a resazurin metabolic assay was performed. 10 scaffolds from each iteration were tested. Resazurin was diluted to 1 mM with phosphate buffered saline (PBS) (pH 7.4). This was diluted further to 0.05 mM solution using the cell culture media. 1 mL of the resazurin solution was placed in each of the 10 wells. The well plate was placed in the incubator for two hours. Using a plate reader, the absorbance at 570/600 nm was measured.

Sonicating Scaffolds seeded with hASCs: Scaffolds containing cells were sonicated using the previously described settings. Half of the scaffolds (n=10) were sonicated for 15 minutes each in cell culture media (DMEM/F12, 10% fetal bovine serum, 1% penicillin-streptomycin) (Thermo Fisher Scientific, Waltham, MA). The remaining scaffolds (n=10) served as controls and were not sonicated. All scaffolds were removed from the incubator during the entire sonication period (3-4 hours).

Picogreen Assay: Picogreen assays were performed on 10 scaffolds from each trial (5 control, 5 sonicated). The assay was performed following the manufacturer's procedure to assess DNA content. The data was also used to normalize the metabolic assay results.

Live/Dead Staining: After sonication, a scaffold from the experimental and control groups were stained with calcein and ethidium. These scaffolds were imaged with a confocal microscope.

Enzyme Degradation: A total of 48 scaffolds were tested. Half of the scaffolds (n=24) were sonicated following the previously described methods for 15 minutes. Half of the sonicated scaffolds and half of the control scaffolds were placed in 1 U/ml enzyme solution (Protease from *Streptomyces griseus*) (n=12 for each group). The remaining scaffolds were placed in PBS. Both the enzyme solution and PBS were changed daily. Every 6 days the scaffolds were rinsed with ultrapure water and placed in an oven at 60° C. for 6-8 hours until fully dry and weighed.

Ultrasound Imaging: Scaffolds that were previously used in enzyme degradation experiments were placed in a Carbopol bath (0.2 w/v %) 27 and were imaged using a imaging transducer. 2D greyscale videos were recorded as the transducer was moved across the surface using the Soft Tissue/MSK settings. All videos were taken at 20% gain. The videos were split into frames and the frames were used to create a maximum intensity projection. The average and most common pixel intensities of the scaffolds were measured, and the background signal was subtracted.

Sonication Through Skin: An adipose tissue sample from a panniculectomy procedure was procured. During testing, the scaffolds (n=12) were placed under the skin above the adipose tissue and sonicated through the skin for 15 minutes. The control scaffolds (n=12) were also placed under the skin for 15 minutes. After testing, the scaffolds were washed with water followed by 1× TE buffer, and then spun in PBS tween to remove adherent cells and proteins from the surface. The scaffolds were weighed before and after testing and SEM images of the surface were taken after testing.

Statistics: A one-way ANOVA test followed by a Tukey's post hoc test was used to determine statistical significance between weight loss and ultrasound period. A mixed effect, generalized linear model was used to determine the effect of vacuum (versus non-vacuum) and ultrasound time (0, 5, 10, or 15 minutes) on dependent variables that characterize material degradation: weight, porosity, compressive modulus measured during the second and third testing cycle, transmittance peak ratios, and weight loss from enzyme degradation. The generalized linear model accounted for heterogeneity in each dependent variable's variance and tested all possible fixed and interactive effects of vacuum and ultrasound time on the dependent variables. The best linear model was chosen using the maximum value of the log-likelihood. Sensitivity analyses were conducted to further investigate effects of vacuum and ultrasound time on each dependent variable separately. To compare resazurin reduction percentages, picogreen DNA concentration, and weight loss from sonicating through the skin, unpaired t tests were used. To compare intensities in ultrasound images a Kruskal-Wallis test was conducted followed by a post hoc Dunn's multiple comparison test. Significance was defined as p<0.05.

In testing the effects of ultrasound exposure time and vacuum/non-vacuum on measures of material degradation, the best statistical model was one that demonstrated an interactive effect between vacuum and the measurement, with significant fixed linear effects of ultrasound exposure periods of 5 and 10 minutes (p<0.0001 for both), but not 15 minutes (p=0.8259). Specifically, in the primary model, ultrasound exposure periods of 5 and 10 minutes led to a significant decrease in compressive modulus, weight, and amide I and II peak ratios, and an increase in porosity and weight loss. Sensitivity analyses demonstrated that vacuum had a significant effect on the amide I and II ratios (p=0.0003), weight (p<0.0001), weight loss (p<0.0001), porosity (p<0.0001), but not on the compressive modulus for each cycle (p=0.93). Further, sensitivity analyses revealed a significant effect of an ultrasound period of 15 minutes on weight (p=0.0001), weight loss (p=0.0001), porosity (p=0.0001), and pore wall thickness for non-vacuumed samples (p=0.028), but not compressive modulus (p=0.50) or amide I and II ratios (p=0.20).

Optimizing Ultrasound Parameters

In preferred embodiments, a 1 MHz fundamental frequency ultrasound wave is modulated with square waves delivering a cluster of 300 pulses at the pulse repetition frequency of 4.5 kHz. Modulation with waves of shapes other than square waves is also contemplated to be within the scope of the invention. Within each pulse, 100 cycles (Cycles per pulse) of the 1 MHz wave is delivered. The cluster of 300 pulses are repeated every 500 ms.

In certain embodiments of the invention, the optimal setting for the period of the cluster of pulses may be between 450 ms and 550 ms. In certain embodiments of the invention, the ultrasound pulses have a duty cycle of between 10% and 15% and preferably between 11.2% and 14.9%. In preferred embodiments, that is, using parameters causing significantly more weight loss compared to other settings, the ultrasound pulses have a 500 ms period and a duty cycle of 13.4%. have a duty cycle of approximately 13.4%. (i.e., the cluster of pulses start every 500 ms and are sustained for approximately 67 ms of the 500 ms period).

Figure 6:
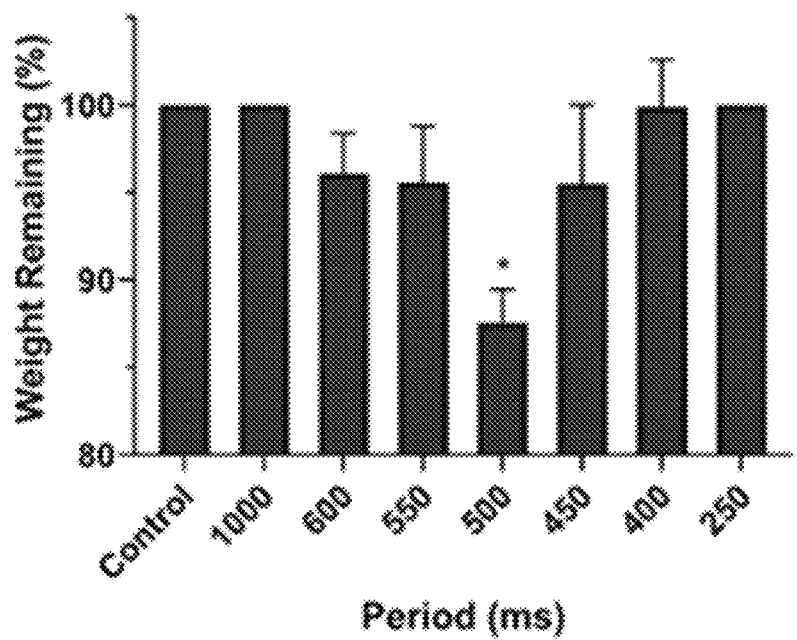
FIG. 6 is a graph showing reduction in weight of various scaffoldings after being exposed to sonication using ultrasonic beam having various periods, showing that using a period of approximately 500 ms results in the most reduction in weight of the scaffold.

To determine if sonication degraded the silk scaffolds, the first metric examined was changes in weight. Weight measurements offer a non-destructive test that could be performed before and after LIFU sonication to optimize ultrasound parameters. The frequency, acoustic amplitude, and intensity parameters were chosen based on settings currently used to disrupt the blood-brain barrier and have been shown to be safe on neurons. Additionally, these parameters are under the FDA imaging ultrasound mechanical index limits, limiting heating and tissue damage. The ultrasound stimulation is applied in pulsed mode rather than delivered continuously, to allow any heat generated to dissipate into the surroundings. To determine the optimum period between pulses, different durations were tested, as shown by the graph in FIG. 6.

Cylindrical silk scaffolds (4 mm diameter×2 mm height) were treated with varying periods of LIFU. A one-way ANOVA followed by a Tukey multiple comparison test was used to determine which groups were significantly different (p<0.05). The asterisks on the graph indicates statistical significance compared to all other groups. Error bars represent standard deviation. Each group had an n=5.

The reason why the 500 ms period was more effective in reducing scaffolds weight is unknown. One interpretation is that this frequency and period combination matches the resonant frequency of silk fibroin. However, there is limited research on the resonant frequency of fibroin and with further analysis it was determined that no changes in the primary or secondary structure of silk fibroin were observed. Another more plausible theory is that the combination of pulse duration and percent duty cycle resulted in the minimum threshold for transient cavitation.

Figure 7A:
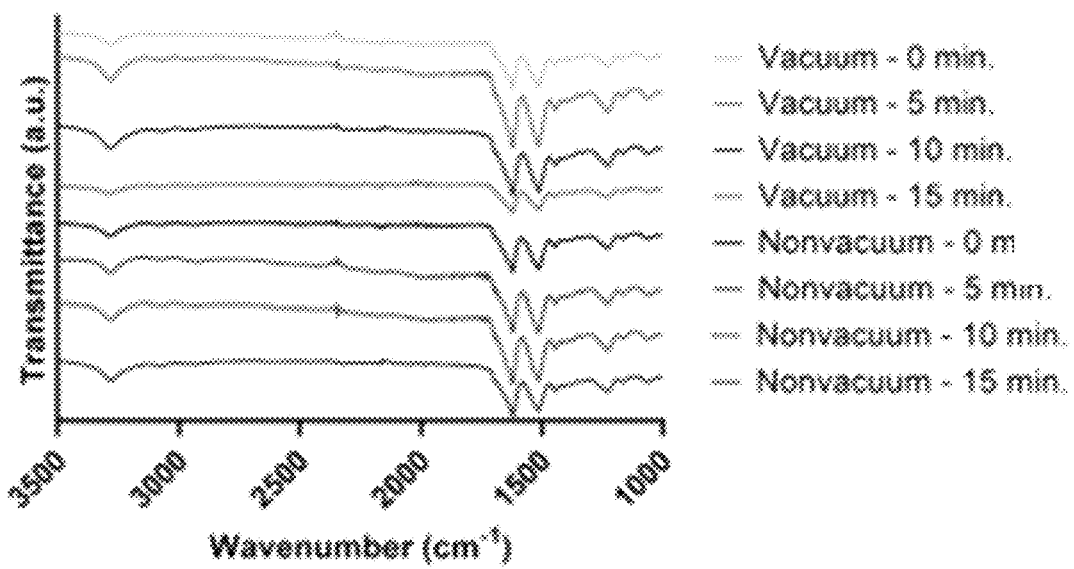
FIGS. 7(A-B) are graphs showing transmittance as a function of wave number of both vacuumed and non-vacuumed scaffoldings.
Figure 7B:
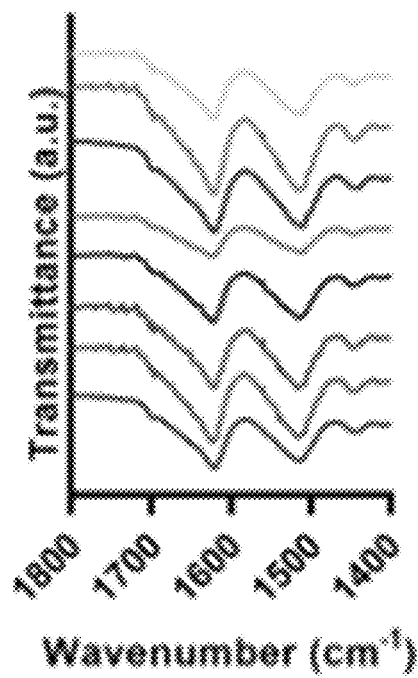

As shown by the graph in FIG. 7(A), after sonication, the scaffolds still exhibited the silk II conformation indicating that ultrasound did not affect the secondary structure. The chemical structure of vacuumed and non-vacuumed samples exposed to 0, 5, 10, and 15 minutes of LIFU was analyzed using attenuated total reflectance (ATR) spectroscopy. The resulting IR spectrums were analyzed to determine the silk conformation for each group. FIG. 7(B) shows a apportion of the IR spectrum seen at higher magnification.

The transmittance ratios were determined by comparing the amide I and amide II peaks with the peak at 3277 $cm^{-1}$ (N-H stretching), termed $T_{amide\ I}/T_{3277}$ and $T_{amide\ II}/T_{3277}$, respectively. This was calculated to determine if the number of bonds differed between sample groups (See FIG. 8(D)). Using mixed effects modeling, it was determined that there was no significant difference between $T_{amide\ I}/T_{3277}$ and $T_{amide\ II}/T_{3277}$ for any control or experimental groups. This indicates that any changes in secondary structure to the amide I and amide II peaks were proportional. However, sonication time was determined to be a factor that caused significant differences in the transmittance ratios. In both the vacuum and non-vacuum groups, there was a significant decrease in transmittance ratio between the 0 min. and 5 min. groups and the 0 min. and 10 min. groups. Removing microbubbles via a vacuum was determined to be another factor that caused significant differences in the transmittance ratios. The vacuumed samples treated with LIFU had significantly higher transmittance ratios compared to the non-vacuumed samples. Though the scaffolds remained primarily in the silk II regime.

Figure 8A:
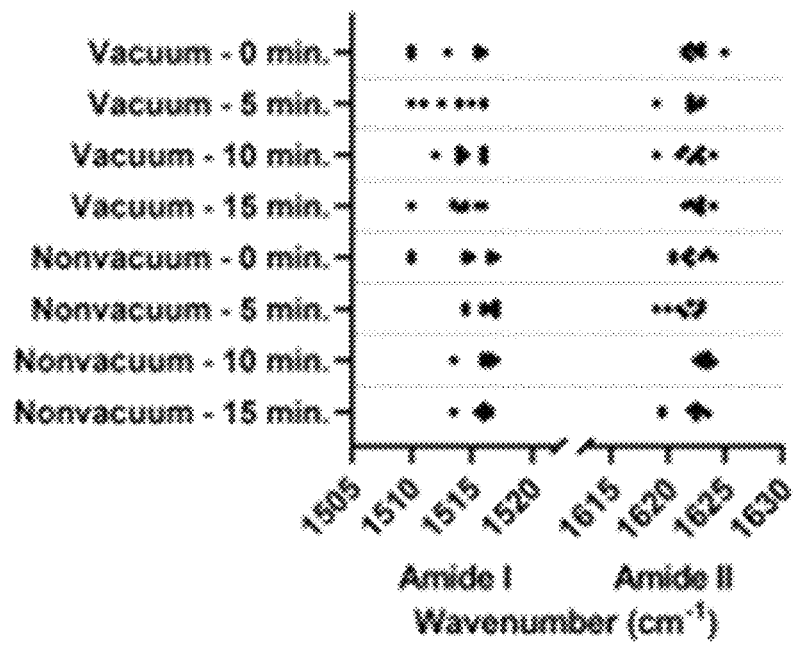
FIG. 8(A) is a graph showing peaks characteristics of the silk secondary structure which are identified in graph for various different scaffolds.
Figure 8B:
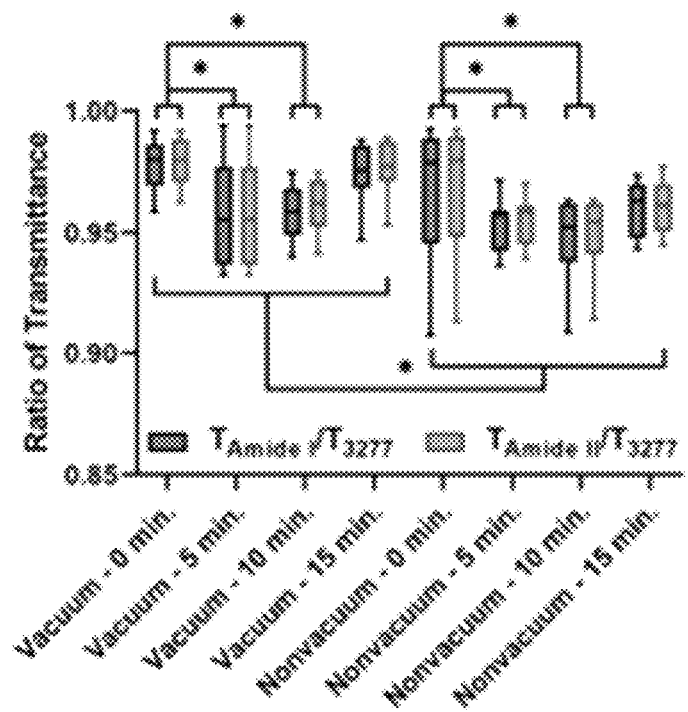
FIG. 8(B) is a graph showing the ratio of transmittance of vacuumed and non-vacuumed scaffolds.

Peaks characteristic of silk's secondary structure (Amide I and Amide II) were identified and graphed for each individual scaffold, as shown in FIG. 8(A). All scaffolds had peaks characteristic of Silk II. In FIG. 8(B), the amide I and amide II peaks were compared to the peak at 3277 $cm^{-1}$ to determine the ratio of transmittance for each group.

An analysis of the percentage of secondary structures (β sheet, β turn, α helix, random coil, and side chains) found in each experimental and control group further supports the conclusion that the secondary structure is not being altered (See FIG. 9(B)). There is no significant difference between secondary structure percentage and scaffold treatment. Though sonication is a technique to induce β sheet formation, there was no significant increase in β sheet percentage. Importantly, there was no change in side group percentages. The side groups play a role in the elasticity and strength of silk. The secondary structures most prevalent in all scaffold groups were β sheet and β turn which is ideal for tissue regenerative applications.

For reference, as shown in FIG. 9(A), the IR ranges for characteristic functional groups for Silk I and Silk II structure are included. As shown in FIG. 9(B), the percentage of secondary structure components was determined from the amide I region of the IR spectrum (N=8 for each group). Experiments were performed in duplicate with independently fabricated scaffolds. Mixed effects modeling was used to determine statistical significance in transmittance ratios. Removal of microbubbles via a vacuum was determined to be a significant factor on the transmittance ratios. There were also statistically significant differences between the 0- and 5-minutes and 0- and 10-minutes groups. Asterisks indicate a p<0.05.

Cell Metabolism and Viability: The therapeutic ultrasound parameters used for the proof-of-concept experiments were chosen because they are below the FDA regulated limits. To verify that the parameters did not have a negative effect on cell metabolism and viability, tissue engineered constructs were tested. hASCs were chosen because the initial intended application of this technique is subcutaneous repair of soft tissue defects.

Figures 10A, 10B:
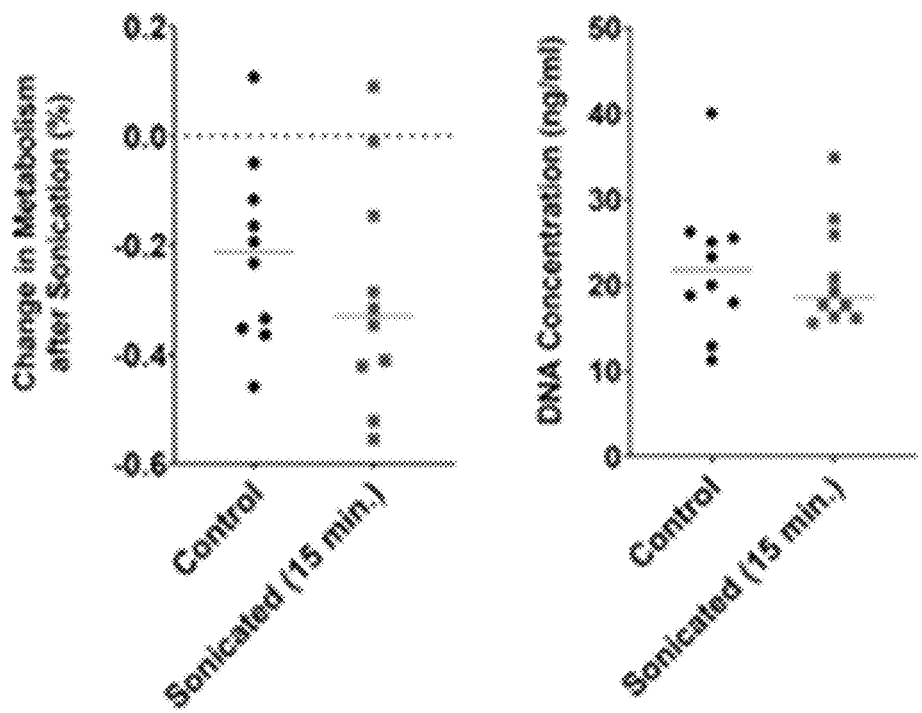
FIGS. 10(A-B) are graphs showing the change in metabolism and the change in DNA, respectively between a control group and a sonicated group after 15 minutes of sonication.

Scaffolds sonicated for 15 minutes showed no significant change compared to the control group indicating that the ultrasound settings did not affect cell viability. To determine if the cellular function was affected by the ultrasound parameters the metabolism was measured before and after sonication using a resazurin assay. Resazurin metabolic assays were performed before and after sonication and the change in metabolism was normalized to DNA content. As shown in FIG. 10(A), each data point represents one scaffold and the solid line indicates the mean of the data. An unpaired t test was performed to determine statistical significance. No significance was detected (p=0.386).

The data was normalized to the DNA content in the scaffolds using a picogreen assay to account for any differences in cell density. DNA content was determined through a picogreen assay. Each data point in FIG. 10(B) represents one scaffold and the solid line indicates the mean of the data. An unpaired t test was performed to determine statistical significance. No significance was detected (p=0.790). As expected, there were no significant differences in viability and DNA content between control and sonicated samples. Comparisons between the first and second trial showed no statistical difference as well. The same number of cells were seeded onto each scaffold, so this signifies that they replicated and grew in a similar manner.

Figures 10C, 10D:
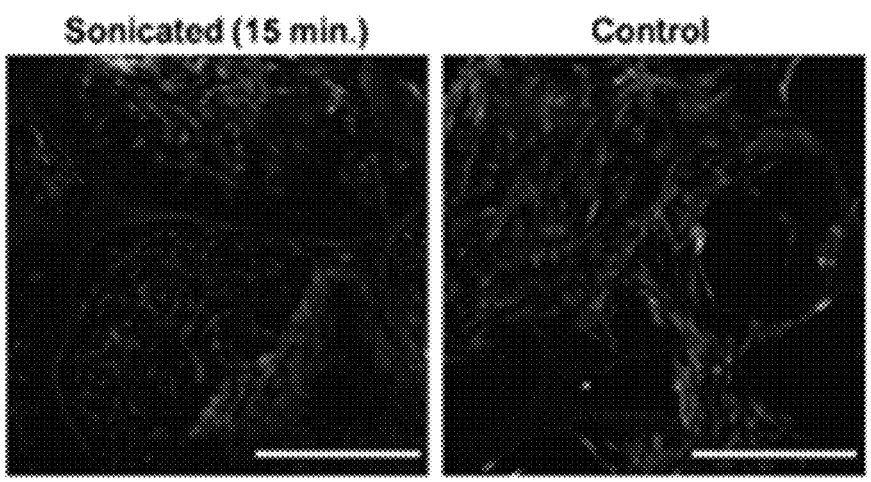

To further confirm viability, after sonication, the experimental group, shown in FIG. 10(C) and the control group, shown in FIG. 10(D), were stained with calcein (stains live cells green) and ethidium (stains dead cells red) to indicate live and dead cells, respectively. Silk scaffolds are also evident in the red channel. Scale bars in the images are 250 μm. Experiments were performed in duplicate with independently fabricated scaffolds. There were no differences between live or dead cells in the control and sonicated samples (silk shows up as red in the image). These results indicate that the ultrasound parameters chosen for testing do not affect the viability or metabolism of hASCs.

Figure 11A:
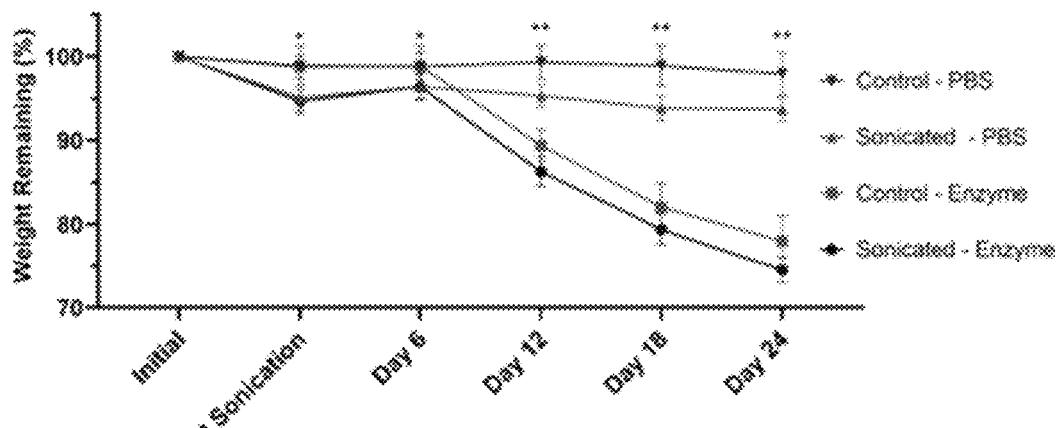
FIG. 11(A) is a graph showing weight loss initially, and in six-day periods showing that scaffolds placed in an enzyme solution lost additional weight after the initial sonication.

Enzymatic Degradation: To test if ultrasound treatments could offset the scaffold degradation profile, a group of control and sonicated scaffolds were placed in either an enzyme or PBS solution. The results are shown in FIG. 11(A). Weight loss was measured every 6 days for 24 days. Sonicated scaffolds lost weight initially while the control scaffolds weight remained constant. The scaffolds placed in an enzyme solution lost weight, with sonicated scaffolds losing the most weight. One scaffold in the control-enzyme group was damaged during drying on day 6 and was not used for further measurements (N=11). N=12 for all other groups and time points. A single asterisk (*) indicates that both control groups were significantly different to both of the sonicated groups. Two asterisks (**) indicate days where all groups are significantly different.

The two groups that were exposed to ultrasound lost about 5% of their mass from the process initially. The sonicated group placed in PBS experienced a significant decrease in weight from sonication and had a constant weight thereafter. Similarly, the control group that was placed in PBS was not significantly different in weight at any timepoint. Scaffolds that were sonicated and then placed in an enzyme solution lost the most weight. The difference between these two groups (~3-4%) remained constant from day 6 to day 24. Starting at day 12, all groups were statistically different when compared to each other. From these results, it can be concluded that sonication significantly offsets the degradation profile but does not change the rate of degradation. In addition, because the relationship between weight loss and ultrasound exposure is linear and weight loss is directly correlated to degradation, the desired degree of degradation can be controlled by choosing ultrasound exposure times.

A two-way ANOVA followed by a Tukey multiple comparison test was used to determine which groups were significantly different. Statistical significance between time points can be seen in the table, where groups with different letters are significantly different p<0.05. Representative ultrasound images from each group: FIG. 11(C) Control-PBS, FIG. 11(D) Control-Enzyme, FIG. 11(E) Sonicated-PBS, and FIG. 11(F) Sonicated-Enzyme. The pixel intensity shown in the graph of FIG. 12(A) of scaffold ultrasound images (N=6) was calculated after 24-days of enzymatic degradation or PBS soaking. The scaffolds that were sonicated and placed in the enzyme solution for 24 days had the lowest average intensity, shown in FIG. 12(A), pixels and the lowest most common pixel intensity, shown in FIG. 12(B), indicating a low overall density. Statistical significance was determined from a Kruskal-Wallis test followed by a Dunn's multiple comparison test. Asterisks (*) indicate significance of p<0.05. Error bars represent standard deviation. Experiments were performed in duplicate with independently fabricated scaffolds.

Figure 11B:
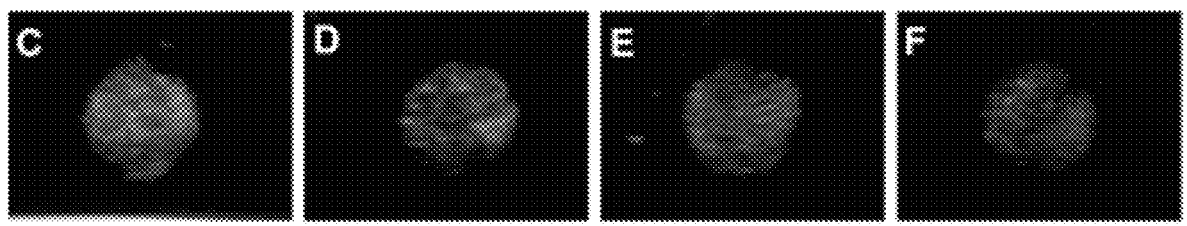
FIG. 11(B) is a table showing the results of a two-way ANOVA followed by a Tukey multiple comparison test to show statistical significance between time points between the groups shown in FIG. 11(A).
Figure 12A:
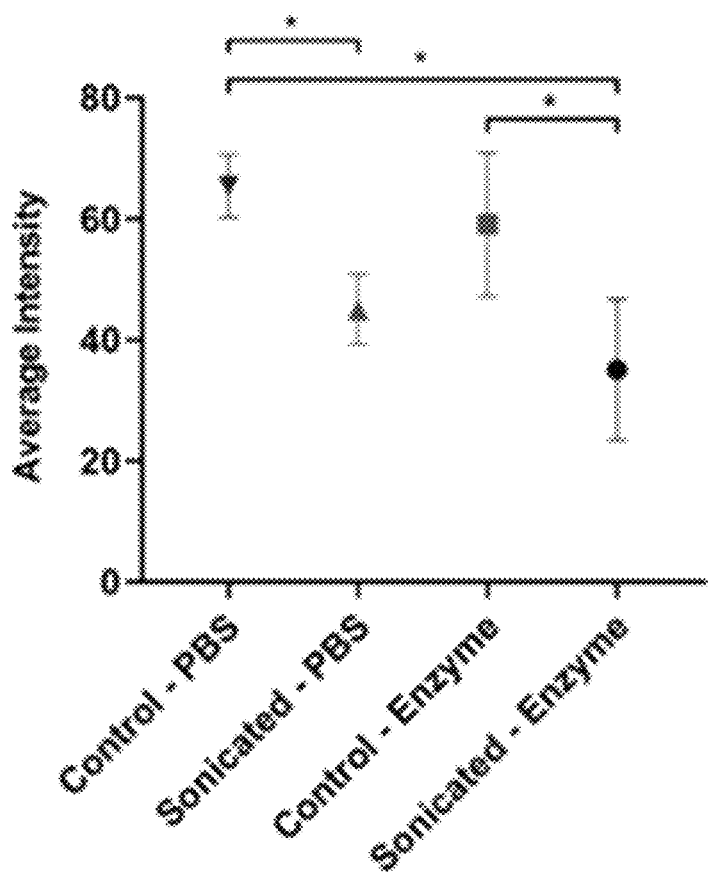
FIGS. 12(A-B) are graphs showing the average pixel intensity in the most common pixel intensity of the ultrasound image is shown in FIGS. 11(C-F).
Figure 12B:
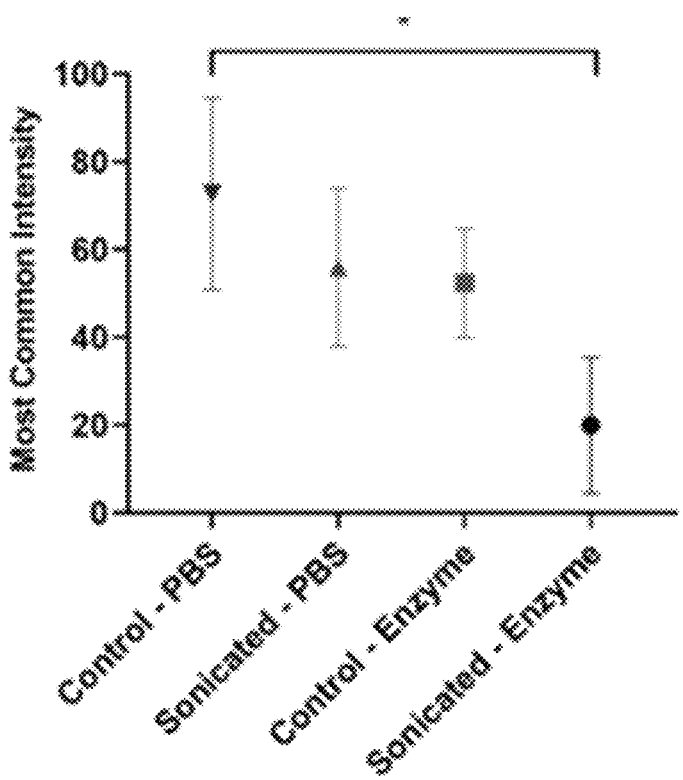

Information regarding scaffold degradation and tissue ingrowth non-invasively in patients can be used to inform clinicians if the scaffold degradation profile needs to be adjusted post-implantation. Researchers have successfully monitored silk hydrogel degradation using ultrasound imaging. To determine if this could be used to monitor scaffold degradation caused by therapeutic ultrasound, the previously described scaffolds were suspended in a Carbopol bath and 2D greyscale ultrasound images were captured and are shown in FIG. 11(C-F). The image intensities were compared as objects with higher acoustic impedance appear lighter in B-mode ultrasound image, as shown in FIG. 12(A,B). Acoustic impedance is dependent on density and the speed of sound. Because the scaffolds were imaged in the same environment, the factor that differs between samples is scaffold density. Thus, the higher density scaffolds will have a greater intensity. As expected, the non-degraded scaffolds had the highest average intensity (neither sonicated nor placed in enzyme). Consistent with the prior results, as shown in FIG. 11(A), the scaffolds sonicated and then placed in an enzymatic solution had the lowest average intensity values (FIG. 11(F)), with a statistically significant difference in intensity value from both control groups. However, the group of scaffolds sonicated and then placed in PBS had the next lowest average intensity. This was surprising because this group lost less weight than the control group placed in enzyme. However, the difference in intensity between the Sonicated-PBS and Control-Enzyme groups was determined not to be statistically significant. Further analysis of the images indicated slight but important differences. The scaffold sonicated, shown in FIG. 11(D), had a greater range in intensities. This is likely due to the ultrasound being focused on the center of the scaffolds and not being delivered uniformly to the entire scaffold. This resulted in the control group placed in enzyme having a narrower range of intensities. By evaluating the most common pixel intensity, shown in the graph of FIG. 12(A), it was determined that the bulk of both scaffolds had similar intensities. These results indicate that the degradation caused by sonication can be observed using 2D greyscale ultrasound imaging. Furthermore, the degradation caused by sonication had a different appearance than enzymatic degradation. Overall, these results suggest that greyscale ultrasound imaging can be paired with therapeutic LIFU to target slower degrading areas of scaffolds.

Figures 13C, 13D:
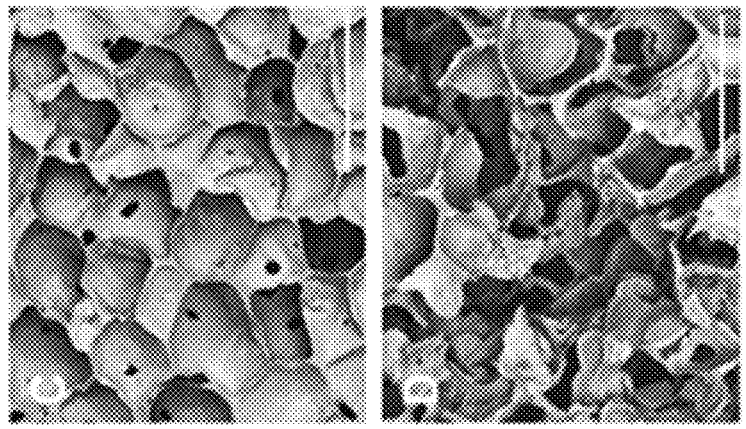
FIG. 13(A) is an image showing an experimental set up wherein scaffolds were implanted in the hypodermis under the skin and thereafter sonicated.
FIG. 13(B) is a graph showing the weight reduction between controlled and sonicated groups.
FIGS. 13(C-D) are SEM images of control and sonicated scaffolds, respectively.

Sonication through Human Skin: To test if these results could be replicated in an ex vivo human subcutaneous implantation model, the silk scaffolds were implanted under the skin in the hypodermal space. The samples were then sonicated through the skin, using the set-up shown in FIG. 13(A), showing the experimental setup wherein scaffolds were implanted in the hypodermis under the skin and were either sonicated for 15 minutes or implanted without sonication as a control. The blue gel is ultrasound transmission gel.

Because weight and surface appearance were two characterization methods that were significantly different between the sonicated and control scaffolds in the previous experiments, these parameters were chosen to evaluate if this approach induced degradation in a similar manner. To mimic any protein adhesion that occurred on the experimental scaffolds, each control scaffold was implanted in the hypodermal space for 15 minutes as well. Because transient cavitation was determined to be the mechanism responsible for scaffold degradation, the samples used in this experiment were not placed under vacuum prior to sonication.

Figure 13B:
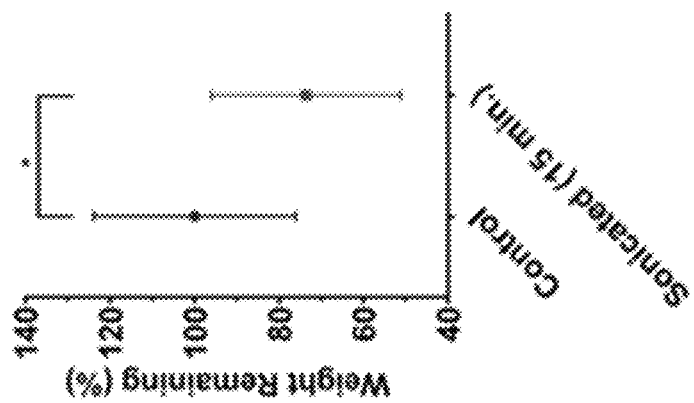
Figure 13A:
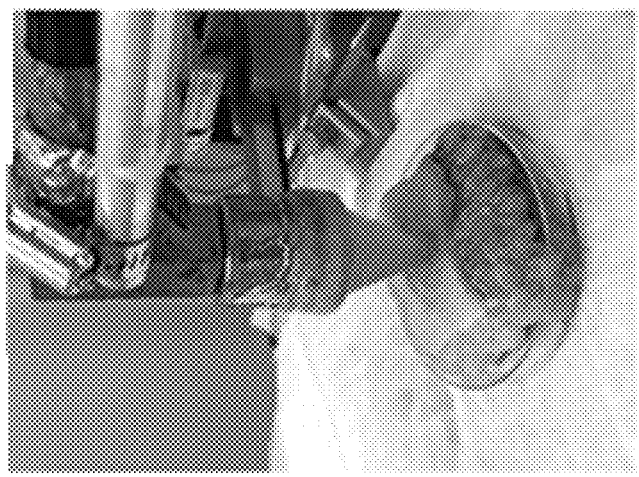

Consistent with the prior experiments, there was a significant amount of weight loss in the sonicated samples versus the control samples, as shown in FIG. 13(B). Scaffolds that were sonicated lost significantly more weight than the control group. This data was normalized to the control to account for any protein adhesion. N=12 for each group. An unpaired t test was performed to determine statistical significance. Significance was detected ($p<0.05$) and is denoted by the asterisk. Error bars represent standard deviation. However, the weight loss was higher than what was seen in the previous experiments, shown in FIG. 6. Multiple factors could be responsible for this enhancement in degradation. First, the ultrasound transducer was more focused (targeting a smaller area of scaffold degradation) in the previous experiments since the collimator was placed as close to the scaffold surface as possible. In the hypodermal implantation experiment, the ultrasound waves travelled through the skin, which caused the waves to be less focused. Second, the material underneath the scaffolds during sonication differed from previous experiments. In the hypodermal experimental setup, the scaffolds were placed above adipose tissue, but in previous experiments the scaffolds were on top of polystyrene. This could have affected the way the ultrasound waves were reflected, potentially causing more weight loss.

The variation in the weight loss is also larger than in previous experiments. This is likely caused by differences in protein adhesion. Scaffolds with higher densities lost more weight compared to the scaffolds with lower densities. Proteins adhering to the surface have a greater effect on scaffolds with lower densities because they have a higher surface to volume ratio. However, the control and sonicated samples have comparable standard deviations. This indicates that implanting the control scaffolds under the skin adequately mimicked the degree of protein adhesion on the scaffolds.

The SEM images shown in FIGS. 13(C,D) further support that ultrasound can be used to degrade scaffolds implanted in the hypodermis. The samples that were sonicated for 15 minutes have visual degradation. FIG. 13(C) is a SEM image of a scaffold that served as the control and was not sonicated. There does not appear to be any structural damage. FIG. 13(D) is a SEM image of a sample that was sonicated for 15 minutes demonstrating visual degradation of the scaffold. In the image in FIG. 13(D), the pore walls appear to be torn and the surface density is significantly lower than the control group shown in the image ion FIG. 13(C), consistent with the images in FIGS. 4(A-D).

Figure 16:
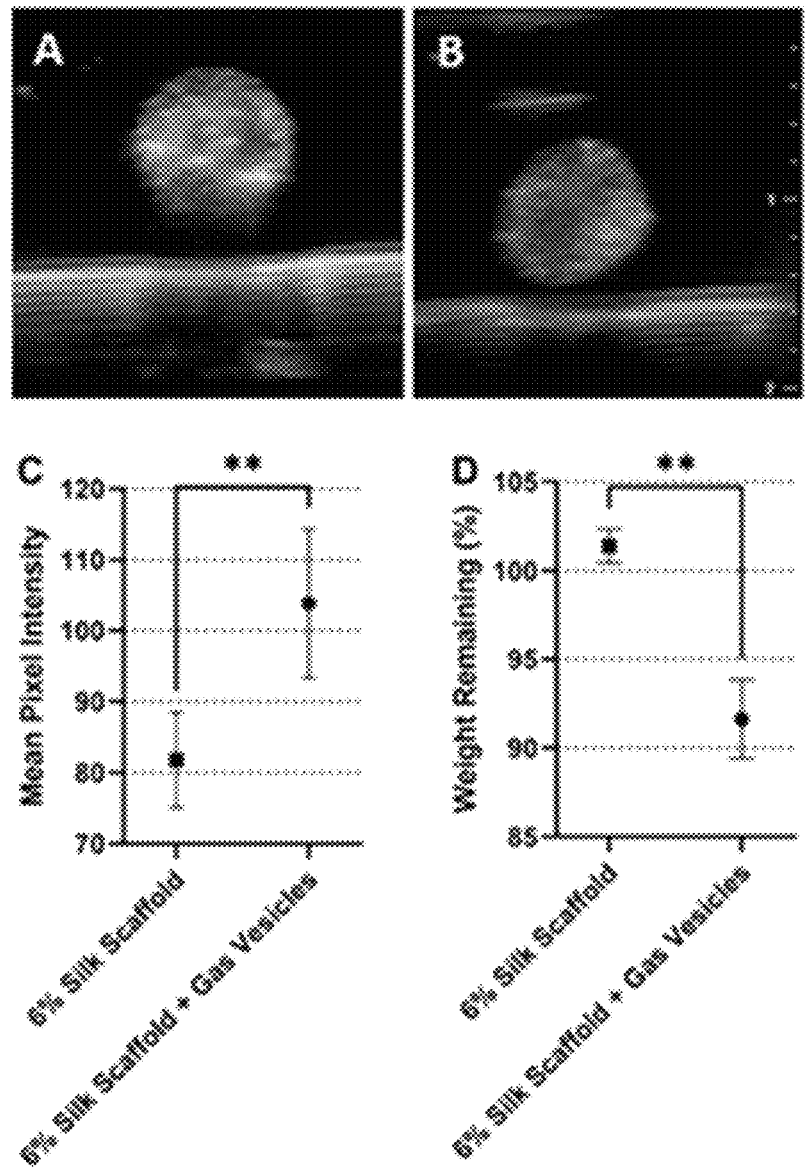
FIG. 16 shows imagery of a second embodiment of the scaffold before and after sonication.

FIG. 16 shows a scaffold of the second embodiment. FIG. 16(A) shows a scaffold 8 mm in diameter. The gas vesicles appear as the brighter portions of the image. In FIG. 16(B), the scaffold shows a lower brightness, indicating the bursting of a portion of the gas vesicles. FIG. 16(C) shows that the average pixel intensity measured to quantify differences in brightness (N=5). FIG. 16(D) shows that, after sonication, scaffolds containing gas vesicles had lost over 9% of their initial weight (N=4). An unpaired t test was performed to determine statistical significance. Significance was detected ($p<0.01$) and is denoted by the two asterisks. Error bars represent standard deviation.

In this work, testing was only performed with the scaffolds placed directly below the skin. Additional research is needed to fully understand the implications of in vivo implantation. Thus, focusing the ultrasound in vivo may require re-optimization of some ultrasound parameters.

This disclosure demonstrates that low-intensity focused ultrasound (LIFU) can be used to trigger degradation of silk scaffolds non-invasively. By comparing weight, porosity, and differences in surface morphology between sonicated and control scaffolds, with and without microbubbles, the mechanism of LIFU degradation was determined to be transient cavitation. Scaffolds seeded with cells experienced no change in metabolism or viability after sonication indicating that the ultrasound parameters were not toxic. 2D greyscale ultrasound imaging was used to detect scaffold degradation, where scaffolds that were sonicated with LIFU had significantly different appearances when compared to control scaffolds. Finally, scaffolds implanted under the skin and sonicated demonstrated similar degradation profiles.

The invention uses focused ultrasound at safe levels to induce reproducible, controllable degradation of silk fibroin scaffolds. The ability to offset degradation of biomaterial scaffolding non-invasively, post-implantation would improve tissue regenerative outcomes by allowing optimization for each patient. Various embodiments of the invention using specific parameters discussed herein as exemplars of the invention, however, the invention is not meant to be limited in scope to the specific parameters mentioned, which may be varied to obtain similar results.

The invention claimed is:

1. A method for creating a silk fibroin tissue scaffold comprising:
   preparing a silk solution comprising silk fibroin extracted from silk cocoons;
   adding a volume of gas vesicles to the silk solution; and
   solidifying the silk solution;
   wherein the gas vesicles are derived from bacteria.

2. The method of claim 1 wherein preparing the silk solution comprises:

boiling the cocoons in an alkali solution to isolate silk fibroin from the cocoons;

dissolving the fibroin in a solution; and performing dialysis on the silk fibroin.

3. The method of claim 1 wherein the gas vesicles are BSA vesicles produced by:

combining a silk solution with bovine serum albumin (BSA);

exposing the solution to heat to dissolve the BSA; and sonicating the silk/BSA solution.

4. The method of claim 3 further comprising:

adding sodium octanoate and N-acetyl-DL-tryptophan to the silk/BSA solution prior to the sonication step.

5. The method of claim 1 wherein the bacteria is *Anabaena flos-aquae* or *Halobacteria salinarum*.

6. The method of claim 1 further comprising:

adding therapeutic cells to the scaffold prior to the solidifying step.

7. The method of claim 6 wherein the therapeutic cells are selected from a group consisting of adipose stem cells, adipocytes, mesenchymal stem cells, osteoblasts and chondrocytes.

8. The method of claim 6 further comprising:

seeding the scaffold with the therapeutic cells; and exposing the scaffold to a growth medium.

9. The method of claim 8 further wherein the growth medium causes the therapeutic cells to fill a majority of free space between the pores of the scaffold.

10. The method of claim 1 further comprising:

adding silk microspheres containing drugs to the scaffold prior to the solidifying step.

* * * * *